US008440613B2

(12) United States Patent (10) Patent No.: US 8,440,613 B2
Harder et al. (45) Date of Patent: May 14, 2013

(54) CONTROLLING DISEASES CAUSED BY TRICHOMONADIDA

(75) Inventors: Achim Harder, Cologne (DE); Gisela Greif, Remagen (DE); Robrecht Froyman, Monheim (DE)

(73) Assignee: Bayer Intellectual Property GmbH (DE)

( * ) Notice: Subject to any disclaimer, the term of this patent is extended or adjusted under 35 U.S.C. 154(b) by 99 days.

(21) Appl. No.: 13/000,871

(22) PCT Filed: Jun. 20, 2009

(86) PCT No.: PCT/EP2009/004474
§ 371 (c)(1),
(2), (4) Date: Dec. 22, 2010

(87) PCT Pub. No.: WO2010/000398
PCT Pub. Date: Jan. 7, 2010

(65) Prior Publication Data
US 2011/0118176 A1 May 19, 2011

(30) Foreign Application Priority Data
Jul. 2, 2008 (DE) .......................... 10 2008 031 283

(51) Int. Cl.
*A61K 31/345* (2006.01)
*A61K 38/12* (2006.01)
(52) U.S. Cl.
USPC ......... 514/4.6; 514/21.1; 514/222.2; 514/449
(58) Field of Classification Search .................. None
See application file for complete search history.

(56) References Cited

U.S. PATENT DOCUMENTS

| | | | |
|---|---|---|---|
| 3,262,930 A | 7/1966 | Herlinger et al. |
| 5,116,815 A | 5/1992 | Takagi et al. |
| 5,514,773 A | 5/1996 | Nishiyama et al. |
| 5,646,244 A | 7/1997 | Nishiyama et al. |
| 5,656,464 A | 8/1997 | Jeschke et al. |
| 5,663,140 A | 9/1997 | Scherkenbeck et al. |
| 5,717,063 A | 2/1998 | Scherkenbeck et al. |
| 5,747,448 A | 5/1998 | Ohyama et al. |
| 5,777,075 A | 7/1998 | Scherkenbeck et al. |
| 5,821,222 A | 10/1998 | Bonse et al. |
| 5,856,436 A | 1/1999 | Nishiyama et al. |
| 5,874,530 A | 2/1999 | Scherkenbeck et al. |
| 6,033,879 A | 3/2000 | Jeschke et al. |
| 6,329,338 B1 | 12/2001 | Sakanaka et al. |
| 2002/0035061 A1 | 3/2002 | Krieger et al. |

FOREIGN PATENT DOCUMENTS
WO WO 2006/053160 * 5/2006

OTHER PUBLICATIONS

Turrens et al. ("Inhibition of *Trypanosoma cruzi* and *T. brucei* NADH fumarate reductase by benznidazole and anthelmintic imidazole derivatives," Molecular and Biochemical Parasitology 82 (1996) 125-129).*

Moraes-Souza et al. ("Strategies for Prevention of Transfusion-Associated Chagas' Disease," Transfusion Medicine Reviews, X (1996) 161-170).*
Stockdale et al. ("Feline Trichomoniasis: An Emerging Disease?" Compendium Vet Jun. 2006 463-476).*
Petrin et al. (Clinical and Microbiological Aspects of *Trichomonas vaginalis*,) Clin Microbiol Rev 11 (1998) 300-317).*
Clark et al. ("Flagellated protozoan infections in turkeys," World Poultry 19 (2003) 1-4).*
Wolfe ("Giardiasis" Clin. Microbiol. Rev. 5 (1992) 93-100).*
Kaminski, R., et al., A New Class of Anthelminitics Effective Against Drug-Resistant Nematodes; Nature Publishing Group, (2008), vol. 452, pp. 176-180.
Harder, A., et al., Chemotherapeutic Approaches to Protozoa; Haemosporina—Current Level of Knowledge and Outlook; Parasitol Res., (2001), 87: pp. 781-784.
Harder, A., et al., Chemotherapeutic Approaches to Protozoa: Giardia, Trichomonas and Entamoeba—Current Level of Knowledge and Outlook; Parasitol Res., (2001), 87: pp. 785-786.
Greif, G., et al., Chemotherapeutic Approaches to Protozoa: Coccidia—Current Level of Knowledge and Outlook; Parasitol Res., (2001), 87: pp. 973-975.
Harder, A., et al., Chemotherapeutic Approaches to Protozoa: Kinetoplastida—Current Level of Knowledge and Outlook; Parasitol Res., (2001), 87: pp. 778-780.
Kulda, J., Trichomonas, Hydrogenosomes and Drug Resistance; International Journal for Parasitology, (1999), 29: pp. 199-212.
Hegngi, F.N., et al., The Effectiveness of Benzimidazole Derivatives for the Treatment and Prevention of Histomonosis (Blackhead) In Turkeys, Veterinary Parasitology, (1999), 81: pp. 29-37.
Von Samson-Himmelstjerna, G., et al., In Vivo Activities of the New Anthelmintic Depsipeptide PF1022A; Parasitol Res., (2000), 86: pp. 194-199.
Nicolay, F., et al., Synergistic Action of a Cyclic Depsipeptide and Piperazine on Nematodes; Parasitol Res., (2000), 86: pp. 982-992.
Harder, A., et al., Cyclooctadepsipeptides—An Anthelmintically Active Class of Compounds Exhibiting a Novel Mode of Action; Int. J. Antimicrobial Agents, (2003), 22: pp. 318-331.
Mehlhorn, H., et al., Effects of a Combination Emodepside and Praziquantel on Parasites of Reptiles and Rodents; Parasitol Res. 97 Suppl, (2005), 1: pp. S64-S69.
Sasaki, T., et al., A New Anthelmintic Cyclodepsipeptide, PF1022A; Journal of Antibiotics, (1992), 45: pp. 692-697.
McDougald, L.R., et al., Blackhead Disease (*Histomonas meleagridis*) Aggravated in Broiler Chickens by Concurrent Infection With Cecal Coccidiosis (*Eimeria tenella*); Avian Diseases, (2001), 45: pp. 307-312.
McDougald, L.R., Blackhead Disease (Histomoniasis) In Poultry: A Critical Review: Avian Diseases, (2005), vol. 49, No. 4, pp. 462-476.
Raether, W., et al., Nitroheterocyclic Drugs With Broad Spectrum Activity; Parasitol Res. (2003), 90: pp. S19-S39.
Bernt, U., et al., Effects of Anthelminthics With Different Modes of Action on the Behavior and Development of *Caenorhabditis elegans*; Fundam. Appl. Nematol., (1998), vol. 21, No. 3., pp. 251-263.
Hu, J., et al., The Efficacy of Some Drugs With Known Antiprotozoal Activity Against *Histomonas meleagridis* in Chickens; Veterinary Parasitology, Elsevier Science, (2004), vol. 121, No. 1, pp. 233-238.

(Continued)

*Primary Examiner* — Christina Bradley

(57) ABSTRACT

The present invention relates to the use of nifurtimox for the treatment of diseases caused by trichomonads, such as, for example, histomoniasis, in particular in turkeys.

20 Claims, No Drawings

OTHER PUBLICATIONS

McKellar, Q.A., et al., Veterinary Anthelminitics: Old and New; Trends in Parasitology: Elsevier Current Trends; (2004), vol. 20, No. 10, pp. 456-461.

Harder, A., et al., Mechanisms of Action of Emodepside; Parasitol Research, (2005), 97; pp. S1-S10.

Monzote, L., A Review of Anti-Parasitic Patents (1988-2008); Recent Patents on Anti-Infective Drug Discovery, (2008), 3: pp. 177-191.

PCT International Search Report Dated Oct. 13, 2009, 8 Pgs.

Adam, R.D., "Biology of *Giardia lamblia*", 2001, Clinical Microbiology Reviews, 14/3:447-475.

Zeledon, R.A., "Chapter 82 Hemoflagellates," 1996, Medical Microbiology, 4th edition, S. Baron, Editor. Galveston (TX): University of Texas Medical Branch at Galveston, 23 pages.

* cited by examiner

CONTROLLING DISEASES CAUSED BY TRICHOMONADIDA

The present invention relates to the use of nifurtimox for the treatment of diseases caused by Trichomonadida and Diplomonadida such as, for example, histomoniasis, in particular in turkeys.

The efficacy of nitro-heterocyclic compounds against protozoan diseases is known in principle (1).

The Protozoa include single-nuclear organisms whose basic structure is a eukaryotic cell. The more precise systematics, however, reveal large differences in habit, morphology and the biochemical metabolism of the individual strains, classes, genera and species. This is why chemicals, depending on their target and active principle, usually do not act equally well against all Protozoa, but only against specific groups of Protozoa (2, 3, 4).

To date, the efficacy of nifurtimox has only been described against protozoan species of the genus *Trypanosoma*, e.g. *Trypanosoma brucei* and *Trypanosoma cruci* (5, DE-AS-1 170 957). *Trypanosoma* have a flagellum which originates on the basal body ("kinetosome", hence order Kinetoplastida) and, in conjunction with the basal body, develops an undulating membrane. *Trypanosoma* grow predominantly in the blood plasma and are transmitted by blood-sucking arthropods. These pathogens cause Chagas disease ("trypanosomiasis") of humans. Nifurtimox is currently almost the only compound which acts against these pathogens. This activity is probably based on inhibiting the enzyme trypanothione reductase, a *Trypanosoma*-specific enzyme. This enzyme is absent in other protozoan pathogens, in particular trichomonads and histomonads.

Within the order Trichomonadida and Diplomonadida, the efficacy of nifurtimox has not been described to date. Trichomonadida are all parasitic Protozoa, for which a plurality of, as a rule 4 to 6, flagella are typical. A pronounced morphological feature is a contractile rod (=costa) within the organisms, which is involved in their movement. In contrast to the Kinetoplastida. Trichomonadida do not have mitochondria, which are important organelles of energy metabolism. Instead, the energy metabolism takes place in what are known as hydrogenosomes. In these organelles, the oxidative decarboxylation of pyruvate is coupled with ATP synthesis and a ferredoxin-controlled electron transport (6). These unicellular parasites multiply by division. No sexual stages or cysts are found. The order Trichomonadida includes many genera (in particular the genera *Trichomonas* and *Histomonas*) and furthermore many species, but most of these are rather harmless and nonpathogenic. However, there are representatives which trigger severe diseases and cause important economical damage in animal keeping. These include the genus *Trichomonas* (in particular *T. gallinae* and *T. gallinarum*), the genus *Tritrichomonas* (in particular *T. foetus* and *T. suis*) and the genus *Histomonas* (in particular *H. meleagridis*).

Trichomonosis of pigeons and of domestic fowl is an infectious disease caused by *Trichomonas gallinae* and *T. gallinarum*. *T. gallinae* parasitizes primarily in the pharynx, in the oesophagus and in the crop. During the course of the disease, however, other organs, mainly liver, heart and lung, are also infested. The infection of young pigeons takes place as early as during the first feeding with pigeon milk from latently infected older animals. Further sources of infection are infested drinking water or feed. The disease is considered the most frequent disease in squabs and causes severe damage, in particular in breeding flocks. Besides the high mortality, symptoms which are observed are digestive disorders, inappetence, reduced consumption of drinking water and feed, and limited ability to fly. *Trichomonas gallinarum* parasitizes in the appendix of chickens and turkeys. The disease causes delayed growth, severe diarrhoea and necrotic inflammation of the liver.

Histomoniasis is an infectious disease which is caused by *Histomonas meleagridis*. Histomonads are gut parasites. Histomoniasis is especially important in turkeys, where it is also referred to as blackhead disease. In turkeys, the disease is caused in particular by the pathogen *Histomonas meleagridis*. Besides turkeys, others which may become infected with the pathogen include chickens, guinea fowl, peacocks, pheasants, partridges and quails, which are also reservoir hosts.

Infection with *Histomonas meleagridis* results in severe inflammation of the appendix and liver, since the pathogen damages the gut tissue and, via the blood, reaches the liver, where it causes the development of necrosis. An accompanying symptom of the disease is frequently circulatory failure, which can be identified by the blackish-blue heads of diseased animals, which gives the disease its name.

In infected flocks, for example in poultry production units, the disease very rapidly spreads to the entire flock and leads to severe economic losses as the result of very high mortality rates (which may be as high as 100%).

Owing to its structural flagella, *Histomonas meleagridis* belongs to the subtribe flagellates (Mastigophora) and to the order Trichomonadida. The flagellate stages multiply in the appendix by division. Starting from the infected appendix, amoeboid-like stages penetrate, via the bloodstream, the liver, which they destroy via large necroses (7).

Transmission of histomonads via the direct route, for example the oral uptake of histomonad-containing fresh faeces, is rare since outside a host the pathogens are only viable for a short time, and since upon passing through the digestive tract, most of them are killed. Tests carried out by American researchers have revealed that in animal experiments infection in turkeys is much more likely to take place via the cloaca than via the oral route. Since the cloaca generates a slight pull after faeces have been deposited, infection via this route is likely to occur under practice conditions, for example via soiled litter. The transmission of pathogens via intermediate hosts has been proven scientifically beyond doubt. It is in particular the caecal worm *Heterakis gallinarum* (eggs or larvae) which is known as vector (in particular as transport vector of *Histomonas meleagridis*). Histomonads may remain infectious up to 4 years in embryonated Heterakis eggs. Further intermediate hosts may be earthworms and arthropods which are contaminated with Heterakis eggs. Another potential risk are chickens and other poultry species. They are less sensitive than turkeys and frequently carry the pathogen without being clinically susceptible; in this way, they contribute to the spreading of the pathogen.

Turkeys can become infected at any age; however, the disease occurs most frequently between age 3 and 12 weeks. The period between infection and appearance of the disease is in most cases 7-12 days. Mortality can be as high as 100% and reaches its maximum on day 17 post-infection. From day 8, infections can be found in the appendix, from day 10 in the liver.

Infected animals are dull, exhausted, their heads and wings droop and they, refuse to eat. The passage of sulphur-coloured droppings, diarrhoea, and later even blood in the stools is typical. The circulatory disorders which are associated with the disease cause a pronounced blackish-blue coloration of the head, which gives the disease its name.

The course of the disease is determined mainly by the age and the intestinal flora of the turkeys. Additional bacterial infections with *E. coli, Clostridium perfringens* or coccidian may aggravate the course (8).

The diagnosis of histomoniasis can be made using native specimens from appendix and liver with the aid of a saline solution. Amoeboid motile stages are discernible under the phase-contrast microscope. PAS staining is used for histological studies.

Up to 1950, arsenic compounds (for example nitarson, carbarson, roxarson) were the only effective compounds against histomoniasis. However, it is known that arsenic compounds are generally not potent enough to treat established infections. A further disadvantage is that their safety index is extremely low: even twice the dosage of roxarson leads to disturbed motor functions in turkeys.

Since 1960, other nitroimidazoles or nitrofurans have been employed, for example in the feed or drinking water, but they have been increasingly banned by the EU and the USA for use in livestock and us feed additives since the mid-90s: dimetridazole was withdrawn from the US market in 1997, and banned for use as feed additive in the EU in 2001. Since Mar. 31, 2003, even nifursol, the only product still licensed in the EU, may no longer be employed owing to safety concerns. Thus, neither pharmaceuticals for therapy nor preparations for the prophylactic control of histomoniasis are available currently and in the future.

The only currently available strategies of avoiding contracting the disease consist in hygiene measures, optimization of the stocking density and of the nutrient supply, and the avoidance of spreading the pathogen. These measures are insufficient and, on their own, cannot prevent infection and disease.

Vaccines against histomoniasis are not available. For example, a vaccination against *Histomonas meleagridis* is biologically impossible since even natural immunity cannot be acquired after infection. Once infected, animals can fall ill again. Attempts to immunize via attenuated live vaccines failed.

There is therefore a need for active substances for the treatment of diseases caused by Trichomonadida, such as, for example, histomoniasis, which active substances have good activity and good toxicological properties.

Surprisingly, we have now found that nifurtimox is active against Trichomonadida, nifurtimox also having good toxicological properties. This activity has not been described to date, and the good toxicological properties have not been expected either.

The Invention Relates to:

The use of nifurtimox for the preparation of pharmaceuticals for the treatment of diseases caused by Trichomonadida.

Nifurtimox is the compound of the formula (I):

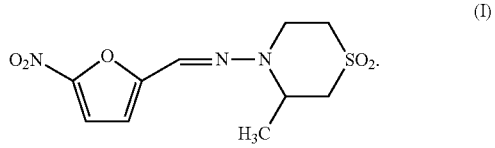 [SMILES: CC1CS(=O)(=O)CCN1N=Cc1ccc([N+](=O)[O-])o1]

If appropriate, the use in the form of customary pharmaceutically acceptable salts is also suitable. If appropriate, the use of hydrates or other solvates of the active substances or, if appropriate, of their salts is furthermore also suitable.

The use can be both prophylactic and therapeutic. The Trichomonadida include the genera *Histomonas, Trichomonas, Tritrichomonas*. From the genus *Trichomonas* there may be mentioned in particular *T. gallinae* and *T. gallinarum*. From the genus *Tritrichomonas* there may be mentioned in particular *T. foetus, T. suis* and *T. equii*. From the genus *Histomonas* there may be mentioned, in particular, *H. meleagridis*.

The Dipomonadida include the genus *Hexamita*. From the genus *Hexamita*, there may be mentioned in particular *H. columbae, H. meleagridis* and *H. salmonis*.

It is preferred to control histomoniasis. It is caused by *Histomonas* spp. It is very especially preferred to control in accordance with the invention histomoniasis caused by *Histomonas meleagridis*. The activity of nifurtimox in the control of histomoniasis is not only directed against the gut-pathogenic stages, but also against the liver stages of the pathogens.

Organisms which are treated in accordance with the invention are animals. Examples which may be mentioned are mammals such as, for example, cattle, horses, pigs, dogs, cats. It is preferred to treat poultry such as, for example, chickens, guinea fowl, partridges, quails, ducks, geese, peacocks, pheasants, pigeons and in particular turkeys (synonymously used for turkey-cocks and turkey-hens).

Examples of Diseases which May be Emphasized are the Following:

Trichomonosis of pigeons, turkeys or of domestic fowl, caused by *T. gallinarum* and/or *T. gallinae*.

Histomoniasis in chickens, guinea fowl, peacocks, pheasants, partridges, quails and in particular in turkeys. Histomoniasis in turkeys (blackhead disease) is caused in particular by *H. meleagridis*.

The active substances are applied directly or in the form of suitable preparations via the enteral, parenteral or dermal route.

The enteral administration of the active substances is effected for example orally in the form of powders, suppositories, tablets, capsules, pastes, drinks, granules, drenches, boluses, medicated feed or drinking water. Dermal administration is effected for example in the form of dipping, spraying, bathing, washing, pouring on and spotting on and dusting. Parenteral administration is effected for example in the form of an injection (intramuscular, subcutaneous, intravenous, intraperitoneal) or by implants.

Suitable Preparations are:

solutions such as solutions for injection, oral solutions, concentrates for oral administration after dilution, solutions for use on the skin or in body cavities, pour-on and spot-on formulations, gels;

emulsions and suspensions for oral or dermal administration and for injection; semi-solid preparations;

formulations in which the active substance is incorporated in an ointment base or in an oil-in-water or water-in-oil emulsion base;

solid preparations such as powders, premixes or concentrates, granules, pellets, tablets, boluses, capsules; aerosols and inhalers, active-substance-containing shaped articles.

Solutions for injection are administered for example intravenously, intramuscularly and subcutaneously.

Oral solutions are administered directly. Concentrates are administered orally after previously having been diluted to the use concentration.

Solutions for use for application to the skin are trickled on, painted on, rubbed on, splashed on, sprayed on or applied by dipping, bathing or washing.

Gels are applied to or painted onto the skin or introduced into body cavities.

Pour-on and spot-on formulations are poured onto or spotted onto limited areas of the skin, the active substance either penetrating the skin and acting systemically or distributing on the body surface.

Emulsions are either of the water-in-oil type or of the oil-in-water type and can be applied orally, dermally or as injections.

Suspensions can be applied orally, dermally or as an injection.

Semi-solid preparations can be administered orally or dermally. They differ from the above-described suspensions and emulsions merely by the fact that they are more viscous.

To prepare solid preparations, the active substances are mixed with suitable excipients, if appropriate with addition of additives, and formulated as desired.

Especially preferred in accordance with the invention is the use in poultry. This is preferably done by oral administration, in particular via medicated feed or the drinking water.

All the abovementioned pharmaceutical forms, the additives and adjuvants to be used and the preparation of these pharmaceutical forms are known in principle to the skilled worker.

The active substances can exist in combination with synergists or with further active substances. Further active substances which may be mentioned are:

Coccidiostats such as robenidine or amprolium, in some cases in combination with folic acid antagonists (for example ethopabate, pyrimethamine, epiroprim);

polyether antibiotics such as monensin, salinomycin, lasalocid, narasin, semduramicin or maduramicin;

triazinones, such as toltrazuril, ponazuril or diclazuril;

sulfonamides (sulfaquinoxalin, sulfadimidin, sulfadiazin).

For a long-time treatment effect, it is recommended to disinfect regularly before housing the animals or after finishing the fattening period.

Helminths, in particular *Heterakis* spp. (larvae) (9) act as transport vectors in the transfer of histomonads. In the treatment of histomoniasis, it may therefore make sense to carry out a combined treatment together with anthelmintics. Thus, it is known that anthelmintics such as, for example, the benzimidazoles albendazole or fenbendazole are prophylactically active in vivo when the treatment is carried out from the time of infection. The usual anthelmintic treatment is for 14 days from the point of time of infection. By a combined treatment together with nifurtimox and anthelmintics, an improved treatment of diseases caused by trichomonads can therefore be achieved.

Anthelmintics which may be mentioned are benzimidazoles such as albendazole, fenbendazole or probenzimidazoles such as febantel. These substances are active for example against *Heterakis* spp., in particulars against *Heterakis gallinarum*, which is known to act as transport vector of *Histomonas meleagridis* (10).

Others which may be mentioned are imidazolethiazoles (levamisol, tetramisol), tetrahydropyrimidines (pyrantel, morantel, oxantel), amidine derivatives, for example amidantel, tribendimidine, and the deacylated amidantel derivative Bay d 9216, and aminoacetonitrile derivatives (see, for example, Kaminsky et al., Nature 452, 176-180 (13 Mar. 2008)), such as, for example, AAD 1470.

Preferred substances which may be mentioned among the anthelmintics are depsipeptide anthelmintics. Depsipeptide anthelmintics such as PF1022A and emodepside have a broad anthelmintic activity against nematodes in various animal species such as gallinaceous birds, rodents, reptiles, dogs, cats, sheep, cattle, goats, horses (11, 12, 13, 14). Here, it has been demonstrated that PF1022A and emodepside are active against nematodes of the superfamily Heterakoidea. These include for example from the family Heterakidae, besides *Heterakis gallinarum* in chickens, the murine nematode *Heterakis spumosa*. PF1022A is active against the latter for example at an oral dose of 50 mg/kg, and emodepside for example in a dose range of 1-10 mg/kg (13, 15). Furthermore, for example PF1022A has been demonstrated to be active against a further representative of the superfamily Heterakoidea, *Ascaridia galli* in chickens, which belongs to the family Ascaridiidae. Here, the compound acts at a dose of 2 mg/kg (16). These substances from the class of the cyclic depsipeptide compounds are therefore suitable for the prophylactic control of, in particular, histomoniasis.

Depsipeptide-anthelmintics which are preferably employed are 24-membered cyclodepsipeptides. The following may be mentioned:

Compounds of the Formula (IIa)

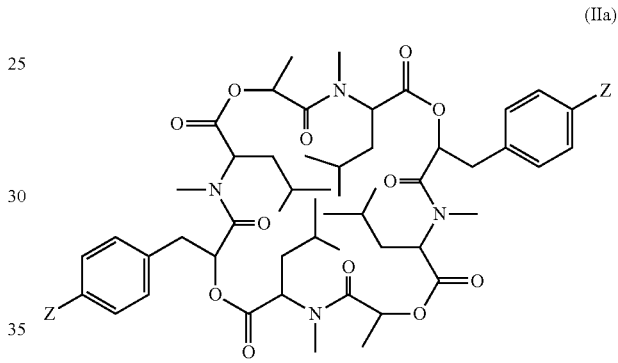

in which

Z represents hydrogen, N-morpholinyl, $NH_2$, mono- or dimethylamino.

Moreover, compounds of the following formula (IIb) may be mentioned:

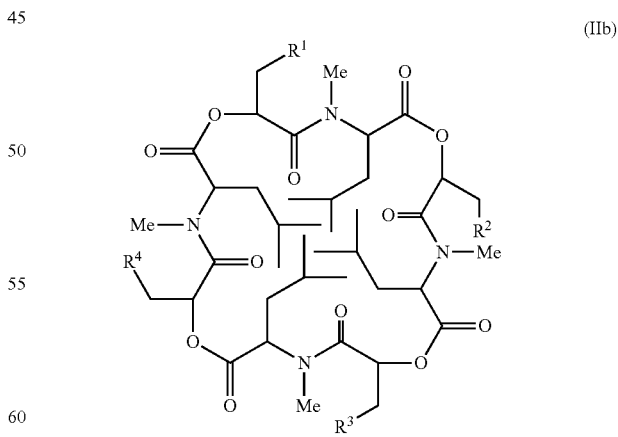

in which $R^1$, $R^2$, $R^3$, $R^4$ independently of one another represent hydrogen, $C_1$-$C_{10}$-alkyl or aryl, in particular phenyl, each of which is optionally substituted by hydroxyl, $C_1$-$C_{10}$-alkoxy or halogen.

The compounds of the general formula (IIb) are known and can be obtained by the processes described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

The cyclic depsipeptides with 24 ring atoms also include compounds of the general formula (IIc)

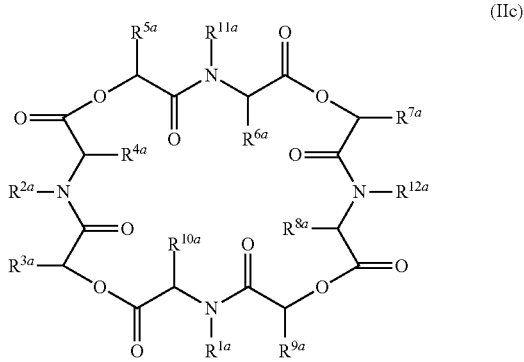

(IIc)

in which
$R^{1a}$, $R^{2a}$, $R^{11a}$ and $R^{12a}$ independently of one another represent $C_{1-8}$-alkyl, $C_{1-8}$-haloalkyl, $C_{3-6}$-cycloalky, aralkyl, aryl,
$R^{3a}$, $R^{5a}$, $R^{7a}$, $R^{9a}$ independently of one another represent hydrogen or a straight-chain or branched $C_{1-4}$-alkyl which can optionally be substituted by hydroxyl, $C_{1-4}$-alkoxy, carboxyl,

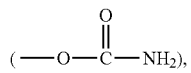

carboxamide, $(-O-\overset{O}{\underset{\|}{C}}-NH_2)$, imidazolyl, indolyl, guanidino, —SH or $C_{1-4}$-alkylthio, and which furthermore represent aryl or aralkyl, each of which can be substituted by halogen, hydroxyl, $C_{1-4}$-alkyl, $C_{1-4}$-alkoxy,
$R^{4a}$, $R^{6a}$, $R^{8a}$, $R^{10a}$ independently of one another represent hydrogen, straight-chain $C_{1-5}$-alkyl, $C_{2-6}$-alkenyl, $C_{3-7}$-cycloalkyl, each of which can optionally be substituted by hydroxyl, $C_{1-4}$-alkoxy, carboxyl, carboxamide, imidazolyl, indolyl, guanidino, SH or $C_{1-4}$-alkylthio, and represent aryl or aralkyl, each of which can be substituted by halogen, hydroxyl, $C_{1-4}$-alkyl, $C_{1-4}$-alkoxy,
and their optical isomers and racemates.

Preferred compounds of the formula (IIe) are those in which $R^{1a}$, $R^{2a}$, $R^{11a}$ and $R^{12a}$ independently of one another represent methyl, ethyl, propyl, isopropyl, n-, s-, t-butyl or phenyl, each of which is optionally substituted by halogen, $C_{1-4}$-alkyl, OH, $C_{1-4}$-alkoxy, and represent benzyl or phenylethyl, each of which can optionally be substituted by the radicals mentioned for phenyl;
$R^{3a}$ to $R^{10a}$ have the abovementioned meanings.

Especially preferred compounds of the formula (IIc) are those in which $R^{1a}$, $R^{2a}$, $R^{11a}$ and $R^{12a}$ independently of one another represent methyl, ethyl, propyl, isopropyl or n-, s-, t-butyl.
$R^{3a}$, $R^{5a}$, $R^{7a}$, $R^{9a}$ represent hydrogen, straight-chain or branched $C_{1-8}$-alkyl, in particular methyl, ethyl, propyl, i-propyl, n-, s-, t-butyl, each of which can optionally be substituted by $C_{1-4}$-alkoxy, in particular methoxy, ethoxy, imidazolyl, indolyl or $C_{1-4}$-alkylthio, in particular methylthio, ethylthio, furthermore represent phenyl, benzyl or phenethyl, each of which can optionally be substituted by halogen, in particular chlorine,
$R^{4a}$, $R^{6a}$, $R^{8a}$, $R^{10a}$ independently of one another represent hydrogen, methyl, ethyl, n-propyl, n-butyl, vinyl, cyclohexyl, each of which can optionally be substituted by methoxy, ethoxy, imidazolyl, indolyl, methylthio, ethylthio, and represent isopropyl, s-butyl, and furthermore represent optionally halogen-substituted phenyl, benzyl or phenylethyl.

The compounds of the formula (IIc) can also be obtained by the processes described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

A very especially preferred depsipeptide which may be mentioned is the compound PF 1022, which is known from EP-OS 382 173; it is the compound of the formula (IIa) in which both substituents Z represent hydrogen. PF 1022 therefore has the following formula (IId):

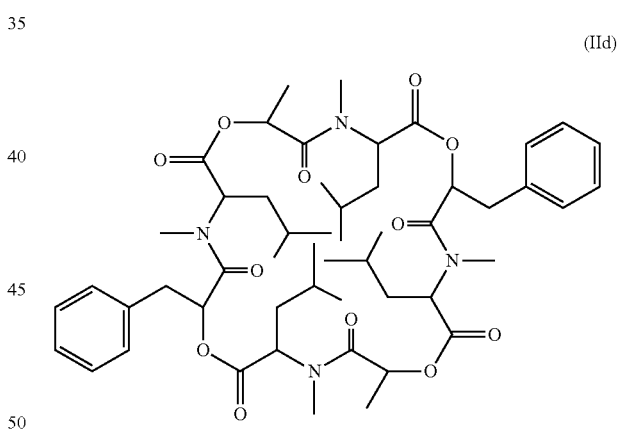

(IId)

Further preferred depsipeptides are compounds which are disclosed in the PCT application WO 93/19053, which are compounds of the formula (IIa)
in which
represents N-morpholinyl, $NH_2$, mono- or dimethylamino.

Very especially preferred among these compounds is the depsipeptide emodepside (PE 1022-221). This is the compound of the formula (IIa) in which both radicals Z represent the morpholinyl radical. The INN emodepside represents the compound with the systematic name: cyclo[(R)-lactoyl-N-methyl-L-leucyl-(R)-3-(p-morpholinophenyl)lactoyl-N-methyl-L-leucyl-(R)-lactoyl-N-methyl-L-leucyl-(R)-3-(p-morpholinophenyl)lactoyl-N-methyl-L-leucyl]. Emodepside is described in WO 93/19053 and has the following formula:

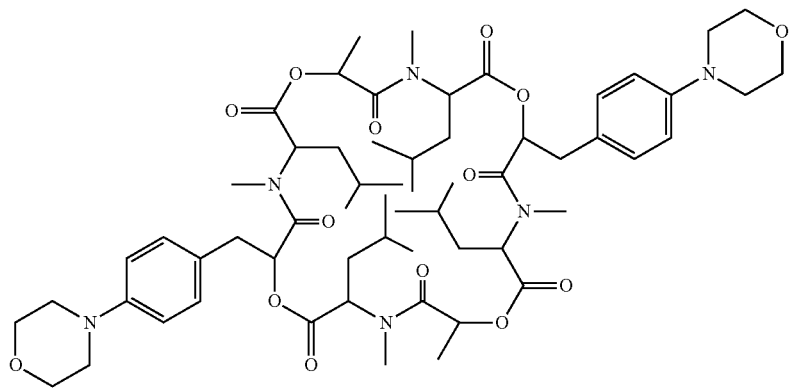 [SMILES: CC(C)CC1C(=O)OC(Cc2ccc(N3CCOCC3)cc2)C(=O)N(C)C(CC(C)C)C(=O)OC(C)C(=O)N(C)C(CC(C)C)C(=O)OC(Cc2ccc(N3CCOCC3)cc2)C(=O)N(C)C(CC(C)C)C(=O)OC(C)C(=O)N1C]

Depending on their structure, the abovementioned active substances which are suitable for the combination may be present in stereoisomeric forms or as stereoisomer mixtures, for example as enantiomers or racemates. Both the stereoisomer mixtures and the pure stereoisomers can be used in accordance with the invention.

The following may furthermore optionally be used: salts of the active substances with pharmaceutically acceptable acids or bases, and also solvates, in particular hydrates, of the active substances or of their salts.

Use in combination means either that nifurtimox and the second active substance, in particular a cyclodepsipeptide, can be employed separately or staggered. In this case, nifurtimox and the second active substance are formulated respectively as a separate pharmaceutical.

The simultaneous use is also feasible. According to a use form which is suitable for this case, the active substances of the combination are formulated together in one composition.

Ready-to-use preparations usually contain the active substance in question in concentrations of 10 ppm to 20% by weight, preferably from 0.1 to 10% by weight.

Preparations which are diluted prior to use contain the active substance in question in concentrations of from 0.5 to 90% by weight, preferably from 5 to 50% by weight. In concentrated solutions for metering into the drinking water, the active substance in question is present for example in concentrations of from 0.5 to 20% by weight, preferably 1 to 15% by weight, especially preferably 2 to 10% by weight.

In general, it has proved advantageous to administer amounts of from approximately 0.05 to approximately 200 mg, preferably from 0.1 to 100 mg, of active substance per kg body weight per clay in order to achieve effective results.

In the mixture with other cocciodiostats or polyether antibiotics, the active substances according to the invention are generally present in the weight ratio 1 to 0.01-50 up to 1 to 1-50.

The active substances can also be administered together with the animals' feed or drinking water.

Feed and foodstuffs contain 0.005 to 1000 ppm, preferably 0.05 to 500 ppm, of the active substance in combination with a suitable edible material.

Such a feed and foodstuff can be used both for therapeutic and for prophylactic purposes.

Such a feed or foodstuff is prepared by mixing, with customary feeds, a concentrate or a premix which comprises 0.5 to 30% by weight, preferably 1 to 20% by weight, of an active substance in admixture with an edible organic or inorganic carrier. Edible carriers are, for example, maize meal or maize and soya meal or mineral salts which preferably comprise a small amount of an edible anti-dust oil, for example maize oil or soya oil. The premix thus obtained can then be added to the complete feed before the latter is fed to the animals.

The Use in Histomoniasis May be Described by Way of Example:

For the curative treatment and prophylaxis of histomoniasis in poultry, in particular in chickens, ducks, geese or turkeys, 0.005 to 1000 ppm, preferably 0.05 to 500 ppm, of an active substance are mixed with a suitable edible material, for example a nutritious feed. If desired, these amounts can be increased, in particular when the active substance is well tolerated by the recipient. The administration via the drinking water can be carried out analogously.

Nevertheless, it may occasionally be necessary to deviate from the abovementioned quantities, in particular as a function of the body weight of the experimental animal or of the type of route of administration, but also depending on the animal species and its individual reaction to the active substance, or on the type of formulation and the time or interval at which it is administered. Thus, it may suffice in some cases to use less than the abovementioned minimum amount, while the mentioned upper limit has to be exceeded in other cases. When larger amounts are administered, it may be expedient to divide them into several individual doses over the course of the day.

The activity of the compounds according to the invention can be demonstrated for example in cage experiments with the following experimental design, where the animals are treated with the respective active substance.

An active-substance-containing feed is prepared in such a way that the required amount of active substance is mixed thoroughly with a nutritionally balanced animal feed, for example with the chick feed specified hereinbelow.

If it is intended to prepare a concentrate or a premix which is eventually to be diluted in the feed to the values mentioned in the experiment, a general procedure is to mix approximately 1 to 30%, preferably approximately 10 to 20% by weight, of active substance with an edible organic or inorganic carrier, for example maize and soya meal or mineral salts, which contain a small amount of an edible de-dusting oil, for example maize oil or soya oil. The premix thus obtained can then be added to the complete poultry feed before being administered.

A suitable example for the use of the substances according to the invention in poultry feed is the following composition:

| | |
|---|---|
| 52.00% | crushed feed grain: 40% maize, 12% wheat |
| 17.00% | extracted soybean meal |
| 5.00% | maize gluten feed |
| 5.00% | wheat feed meal |
| 3.00% | fish meal |
| 3.00% | mineral blend |
| 3.00% | lucerne-grass meal |
| 2.50% | vitamin blend |
| 2.00% | comminuted wheat germs |
| 2.00% | soya oil |
| 2.00% | meat-bone meal |
| 1.50% | powdered whey |
| 1.00% | molasses |
| 1.00% | brewer's yeast mixed with spent grain |
| 100.00% | |

Such a feed contains 18% crude protein, 5% crude fibre, 1% Ca. 0.7% P and, per kg, 1200 IU vitamin A, 1200 IU vitamin D3, 10 mg vitamin E, 20 mg zinc bacitracin.

REFERENCES

1. Raether W., Hänel H. (2003): Nitroheterocyclic drugs with broad spectrum activity Parasitol Res. 90:19-39.
2. Harder A., Greif G., Haberkorn A. (2001a): Chemotherapeutic approaches to protozoa: Haemosporina—current level of knowledge and outlook.
3. Harder A. Greif G. Haberkorn A. (2001b): Chemotherapeutic approaches to protozoa: *Giardia, Trichomonas* and *Entamoeba*—current level of knowledge and outlook.
4. Greif G. Harder A., Haberkorn A. (2001): Chemotherapeutic approaches to protozoa: Coccidia—current level of knowledge and outlook.
5. Harder A., Greif G., Haberkorn A. (2001c): Chemotherapeutic approaches to protozoa: Kinetoplastida—current level of knowledge and outlook. Parasitol Res 87:778-780.
6. Kulda J. (1999): *Trichomonas*, hydrogenosomes and drug resistance. International Journal for Parasitology 29: 199-212.
7. McDougald L. R. (2005): Blackhead Disease (Histomoniasis) in Poultry: A critical Review. Avian Diseases 49 (4):462-476.
8. McDougald, Hu. J. (2001): Blackhead Disease (*Histomonas meleagridis*) aggravated in broiler chickens by concurrent infection with cecal coccidiosis (*Eimeria tenella*). Avian Diseases 45:307-312.
9. Hegngi F. N. Doerr J., Cummings T. S., Schwartz R. D., Saunders G., Zajac A., Larsen C. T., Piierson F. W. (1999): The effectiveness of benzimidazole derivatives for the treatment and prevention of histomonosis (blackhead) in turkeys. Veterinary Parasitology 81:29-37.
10. Hegngi, F. N., Doeerr, J., Cummings, T. S., Schwartz, R. D., Saunders. G., Zajac, A., Larsen, C. T., Pierson. F. W. (1999): The effectiveness of benzimidazole derivatives for the treatment and prevention of histomonosis (blackhead) in turkeys. Veterinary Parasitology 81:29-37.
11. von Samson-Himmelstjerna G., Harder A., Schnieder T. Kalbe J. Mencke N. (2000): In vivo activities of the new anthelmintic depsipeptide PF1022A. Parasitol. Res. 86:194-199.
12. Mehlhorn H., Nicolay F., Harder A., von Samson-Himmelstjerna A. (2000): Synergistic action of Bay 44-4400 and piperazine on nematodes of the mouse in vitro and in vivo: a light and transmission electron microscopic study. Parasitol. Res. 86:982-992.
13. Harder A. Schmitt-Wrede H.-P., Krücken J., Marinovski P., Wunderlich F., Willson J., Amliwala K., Holden-Dye L., Walker R. (2003): Cyclooctadepsipeptides—an anthelmintically active class of compounds exhibiting a novel mode of action. Int. J. Antimicrobial Agents 22:318-331.
14. Mehlhorn H., Schmahl G., Frese M., Mevissen I., Harder A., Krieger K. (2005): Effects of a combination emodepside and praziquantel on parasites of reptiles and rodents. Parasitol. Res. 97 Suppl 1:65-69.
15. Bernt U., Junkersdorf. B., Londershausen M., Harder A., Schierenberg E. (1998): Effects of anthelmintics with different modes of action on the behaviour and development of *Caenorhabditis elegans*. Fundam. Appl. Nematol. 21:251-263.
16. Sasaki T. Takagi M, Yaguchi T, Miyadoh S, Okada T. Koyama S (1992): A new anthelmintic cyclodepsipeptide, PF1022A. Journal of Antibiotics 45:692-697.

EXAMPLES

Medicated Feed

Medicated feeds can be prepared by admixing pulverulent nifurtimox in concentrations of 50, 100, 200 and 400 ppm to the feed mix detailed hereinbelow.

| | |
|---|---|
| 52.00% | crushed feed grain: 40% maize, 12% wheat |
| 17.00% | extracted soybean meal |
| 5.00% | maize gluten feed |
| 5.00% | wheat feed meal |
| 3.00% | fish meal |
| 3.00% | mineral blend |
| 3.00% | lucerne-grass meal |
| 2.50% | vitamin blend |
| 2.00% | comminuted wheat germs |
| 2.00% | soya oil |
| 2.00% | meat-bone meal |
| 1.50% | powdered whey |
| 1.00% | molasses |
| 1.00% | brewer's yeast mixed with spent grain |
| 100.00% | |

Tablets

Nifurtimox tablets are known and available as a pharmaceutical for example under the trade name Lampit®.

A. Biological Example

Cage Experiments; Histomonad-Activity in Turkeys

Histomonad-free male turkeys aged 10 days received nifurtimox or the comparative compound nitarson in the concentration given in "ppm" together with the feed from day −4 (=4 days prior to infection) to day 14. Infection is carried out on day 0, 10 animals are kept per group cage. 1 to 3 such groups are employed per dose.

The infection is carried out with a histomonad field strain which is passaged in the laboratory and stored in liquid nitrogen. On day 0, in each case 5 animals of a cage (with the exception of the noninfected control) are infected intracloacally with 250 000 histomonads in each case 1 ml of Dwyer's medium (=direct infection). After a few days, these infected animals excrete fresh histomonads and thus transmit the pathogen to the remaining 5 animals of the cage (=indirect infection).

To assess the activity, the criteria of McDougald and Hu 2001 (7) are taken into consideration:
- the infection-caused mortality
- the weight gain from the beginning to the end of the experiment
- feed consumption
- feed conversion
- macroscopic assessment of the infection-related lesions in the appendices (caecum) and in the liver. In this assessment, score 0=no lesions and score 4=severe lesions.

TABLE 1

Study design 210 animals

| | | Treatment | | | |
|---|---|---|---|---|---|
| Group | Code | Compound | Concentration | Day | Infection |
| Uninf. | D | untreated | — | — | − |
| Inf. contr. | F | untreated | — | — | + |
| 30 ppm | E | nifurtimox | 30 ppm | −4 to +14 | + |
| 60 ppm | B | nifurtimox | 60 ppm | −4 to +14 | + |
| 120 ppm | C | nifurtimox | 120 ppm | −4 to +14 | + |
| 200 ppm | G | nifurtimox | 200 ppm | −4 to +14 | + |
| Nita. | A | nitarsone | 187.5 ppm | −4 to +14 | + |

TABLE 2

Study design 210 animals

| | | Treatment | | | |
|---|---|---|---|---|---|
| Group | Code | Compound | Concentration | Day | Infection |
| Uninf. | G | untreated | — | — | − |
| Inf. contr. | A | untreated | — | — | + |
| 100 ppm | D | nifurtimox | 100 ppm | −4 to +14 | + |
| 200 ppm | F | nifurtimox | 200 ppm | −4 to +14 | + |
| 300 ppm | B | nifurtimox | 300 ppm | −4 to +14 | + |
| 400 ppm | C | nifurtimox | 400 ppm | −4 to +14 | + |
| Nita. | E | nitarsone | 187.5 ppm | −4 to +14 | + |

TABLE 3

Mortality caused by histomoniasis

| Treatment | Mortality | Treatment | Mortality |
|---|---|---|---|
| inf. contr. | 7 | inf. contr. | 11 |
| 30 ppm | 5 | 100 ppm | 13 |
| 60 ppm | 6 | 200 ppm | 4 |
| 120 ppm | 5 | 300 ppm | 2 |
| 200 ppm | 4 | 400 ppm | 0 |
| Nita. | 1 | Nita. | 2 |

TABLE 4

Mean weight gain (g) between day 0 and the time of death

| | Direct infection | | | Direct infection | |
|---|---|---|---|---|---|
| Treatment | no | yes | Treatment | no | yes |
| Uninf. | 791 | | uninf. | 819 | |
| Inf. contr. | 741 | 197 | inf. contr. | 666 | 259 |
| 30 ppm | 730 | 235 | 100 ppm | 581 | 135 |
| 60 ppm | 838 | 304 | 200 ppm | 525 | 270 |
| 120 ppm | 744 | 182 | 300 ppm | 750 | 450 |
| 200 ppm | 744 | 264 | 400 ppm | 832 | 691 |
| Nita. | 782 | 541 | Nita. | 725 | 426 |

TABLE 5

Mean feed consumption between day 0 and day 14

| Treatment | Feed consumption (kg) | Treatment | Feed consumption (kg) |
|---|---|---|---|
| Uninfected control | 12.01 | Uninfected control | 12.44 |
| Infected control | 8.84 | Infected control | 9.56 |
| 30 ppm | 9.00 | 100 ppm | 6.69 |
| 60 ppm | 9.68 | 200 ppm | 9.14 |
| 120 ppm | 8.70 | 300 ppm | 10.40 |
| 200 ppm | 9.59 | 400 ppm | 11.79 |
| Nita. | 11.64 | Nita. | 9.82 |

TABLE 6

Mean feed conversion between day 0 and day 14

| Treatment | Feed conversion | Treatment | Feed conversion |
|---|---|---|---|
| Uninfected control | 1.52 | Uninfected control | 1.63 |
| Infected control | 1.89 | Infected control | 2.10 |
| 30 ppm | 1.88 | 100 ppm | 2.32 |
| 60 ppm | 1.70 | 200 ppm | 2.33 |
| 120 ppm | 1.88 | 300 ppm | 1.83 |
| 200 ppm | 1.91 | 400 ppm | 1.55 |
| Nita. | 1.77 | Nita. | 1.79 |

TABLE 7

Average lesions in the appendix

| | Direct infection | | | Direct infection | |
|---|---|---|---|---|---|
| Treatment | no | yes | Treatment | no | yes |
| Uninfected control | 0.03 | | Uninfected control | 0.00 | |
| Infected control | 0.29 | 3.93 | Infected control | 0.93 | 2.93 |
| 30 ppm | 0.29 | 3.73 | 100 ppm | 1.08 | 3.79 |
| 60 ppm | 0.00 | 3.53 | 200 ppm | 1.80 | 3.67 |
| 120 ppm | 0.53 | 4.00 | 300 ppm | 0.79 | 2.53 |
| 200 ppm | 0.47 | 3.80 | 400 ppm | 0.27 | 1.20 |
| Nita. | 0.00 | 2.26 | Nita. | 0.29 | 3.07 |

TABLE 8

Infection-related lesions in the liver

| | Direct infection | | | Direct infection | |
|---|---|---|---|---|---|
| Treatment | no | yes | Treatment | no | yes |
| Uninf. | 0.00 | | uninf. | 0.00 | |
| Inf. contr. | 0.29 | 3.47 | inf. contr. | 0.14 | 1.80 |
| 30 ppm | 0.29 | 2.53 | 100 ppm | 0.58 | 2.00 |
| 60 ppm | 0.00 | 2.53 | 200 ppm | 0.73 | 1.33 |
| 120 ppm | 0.27 | 1.80 | 300 ppm | 0.07 | 0.40 |
| 200 ppm | 0.13 | 1.33 | 400 ppm | 0.00 | 0.00 |
| Nita. | 0.00 | 0.13 | Nita. | 0.21 | 0.79 |

B. Biological Example

Anthelmintic Properties of the Cyclic Octadepsipeptides

Male mice (strain Bor CFW, body weight between 25 and 30 g) are kept in Makrolon cages (3 animals/cage) and fed ad lib with water and SNIFF rat food (10 mm pellets). Mice are infected with *Heterakis spumosa* by oral administration of 90 embryonated eggs. The eggs had been obtained from female worms which had been isolated from the mices colon 40 days post-infection. The eggs were incubated for a further 3 weeks at 37° C. 35 days post-infection, the mice were treated with the respective dose of PF1022A or emodepside on four consecutive days. PF1022A is suspended in Cremophor EL. On day 7 after the treatment, the mice are sacrificed, the ileum/caecum/colon region is removed, and the worms are counted with the naked eye. The ratio of the number of expelled worms in percent of the total number of worms in untreated, infected control animals is defined as the measure for the anthelmintic activity.

The experiments on chickens are described in (14) and the literature cited therein.

TABLE 9

Anthelmintic activity of PF1022A and emodepside against nematodes from the superfamily *Heterakoidea*

| Nematode | Dose with full activity |
| --- | --- |
| PF1022A | |
| *Heterakis spumosa* (mouse) | 50 mg/kg |
| *Ascaridia galli* (chicken) | 2 mg/kg |
| Emodepside | |
| *Heterakis spumosa* (mouse) | 1-10 mg/kg |

The invention claimed is:

1. A method of treating a disease caused by a Trichomonadida species in an animal comprising administering to the animal in need thereof a pharmaceutical formulation comprising nifurtimox.

2. A method of treating a disease caused by a Histomonad in an animal comprising administering to the animal in need thereof a pharmaceutical formulation comprising nifurtimox.

3. The method of claim 2, wherein the Histomonad is *Histomonas meleagridis*.

4. The method of claim 1, wherein the Trichomonadida species is of the genus *Trichomonas*.

5. The method of claim 1, wherein the Trichomonadida species is of the genus *Tritrichomonas*.

6. The method of claim 1, wherein the pharmaceutical formulation further comprises an anthelmintic.

7. The method of claim 6, wherein the anthelmintic comprises a cyclodepsipeptide.

8. The method of claim 3 wherein the cyclodepsipeptide comprises a compound selected from the group consisting of PF1022, PF1022A, PF1022-221, salts thereof, and solvates thereof.

9. The method of claim 6, wherein the anthelmintic comprises a benzimidazole or probenzimidazole.

10. The method of claim 1, wherein the animal is poultry.

11. The method of claim 1, wherein the pharmaceutical formulation comprising nifurtimox is administered orally to the animal.

12. The method of claim 11, wherein the pharmaceutical formulation comprising nifurtimox is administered to the animal by mixing into the animal's feed or drinking water.

13. The method of claim 2, wherein the pharmaceutical formulation further comprises an anthelmintic.

14. The method of claim 13, wherein the anthelmintic comprises a cyclodepsipeptide.

15. The method of claim 14 wherein the cyclodepsipeptide comprises a compound selected from the group consisting of PF1022, PF1022A, PF1022-221, salts thereof, and solvates thereof.

16. The method of claim 13, wherein the anthelmintic comprises a benzimidazole or probenzimidazole.

17. The method of claim 2, wherein the animal is poultry.

18. The method of claim 2, wherein the animal is a turkey.

19. The method of claim 2, wherein the pharmaceutical formulation comprising nifurtimox is administered orally to the animal.

20. The method of claim 19, wherein the pharmaceutical formulation comprising nifurtimox is administered to the animal by mixing into the animal's feed or drinking water.

* * * * *